US 9,297,255 B2

(12) United States Patent
Gao et al.

(10) Patent No.: US 9,297,255 B2
(45) Date of Patent: Mar. 29, 2016

(54) NON-INVASIVE COMPRESSIBILITY AND IN SITU DENSITY TESTING OF A FLUID SAMPLE IN A SEALED CHAMBER

(75) Inventors: Li Gao, Katy, TX (US); Mark A. Proett, Missouri, TX (US); Sami Eyuboglu, Conroe, TX (US); Tony Herman van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 66 days.

(21) Appl. No.: 13/389,583

(22) PCT Filed: Jun. 17, 2010

(86) PCT No.: PCT/US2010/039050
§ 371 (c)(1),
(2), (4) Date: Mar. 30, 2012

(87) PCT Pub. No.: WO2011/159304
PCT Pub. Date: Dec. 22, 2011

(65) Prior Publication Data
US 2013/0199286 A1    Aug. 8, 2013

(51) Int. Cl.
G01N 9/04       (2006.01)
G01N 33/28      (2006.01)
E21B 49/08      (2006.01)

(52) U.S. Cl.
CPC .............. *E21B 49/08* (2013.01); *E21B 49/081* (2013.01); *G01N 9/04* (2013.01); *G01N 33/2823* (2013.01); *E21B 2049/085* (2013.01)

(58) Field of Classification Search
CPC . E21B 49/081; E21B 2049/085; E21B 49/08; G01N 33/2823; G01N 9/04

USPC ................. 73/54.01, 152.18, 152.51
See application file for complete search history.

(56) References Cited

U.S. PATENT DOCUMENTS

| 2,945,677 | A | * | 7/1960 | Kammerer, Jr. | ................. 60/431 |
| 3,442,135 | A | * | 5/1969 | Liu | .................. 73/744 |
| 3,881,345 | A | * | 5/1975 | Souder | ............................ 73/820 |
| 3,930,403 | A | * | 1/1976 | Cross et al. | .................. 73/54.07 |
| 4,562,726 | A | * | 1/1986 | Barnaby | ........................... 73/38 |
| 4,924,695 | A | * | 5/1990 | Kolpak | ........................ 73/19.01 |
| 5,231,352 | A |   | 7/1993 | Huber | |

(Continued)

FOREIGN PATENT DOCUMENTS

| CN | 1107231 | 8/1995 |
| CN | 1947005 | 4/2007 |

OTHER PUBLICATIONS

PCT/US2010/039050 International Search Report and Written Opinion, Mar. 22, 2011 (8 p.).

(Continued)

*Primary Examiner* — John Fitzgerald
(74) *Attorney, Agent, or Firm* — Chamberlain Hrdlicka

(57) ABSTRACT

In situ density and compressibility of a fluid sample are determined for a fluid sample collected downhole. The density and compressibility of the fluid sample is determined by measuring a distance to a piston contained within the sample chamber using an external magnetic field sensor that senses a magnetic field emanating from a magnetic provided on the piston internal to the sample chamber. The testing is performed quickly and at the surface in a noninvasive fashion (i.e., without opening the sample chamber).

5 Claims, 6 Drawing Sheets

(56) References Cited

U.S. PATENT DOCUMENTS

| | | | |
|---|---|---|---|
| 5,473,939 A * | 12/1995 | Leder et al. | 73/152.12 |
| 5,509,299 A | 4/1996 | Sarvazjan et al. | |
| 5,589,650 A * | 12/1996 | Flemming et al. | 73/866 |
| 5,747,674 A * | 5/1998 | Moracchini et al. | 73/61.44 |
| 6,334,489 B1 * | 1/2002 | Shwe et al. | 166/250.01 |
| 6,640,625 B1 | 11/2003 | Goodwin | |
| 6,672,386 B2 * | 1/2004 | Krueger et al. | 166/252.5 |
| 6,997,683 B2 * | 2/2006 | Allington et al. | 417/18 |
| 7,011,155 B2 * | 3/2006 | Meister et al. | 166/250.01 |
| 7,140,436 B2 * | 11/2006 | Grant et al. | 166/264 |
| 7,198,105 B2 * | 4/2007 | Grant et al. | 166/305.1 |
| 7,216,533 B2 * | 5/2007 | McGregor et al. | 73/152.27 |
| 2004/0045706 A1 * | 3/2004 | Pop et al. | 166/250.07 |
| 2004/0231842 A1 * | 11/2004 | Shammai et al. | 166/264 |
| 2005/0268709 A1 * | 12/2005 | McGregor et al. | 73/152.27 |
| 2006/0070426 A1 * | 4/2006 | Pelletier | 73/54.02 |
| 2007/0214877 A1 * | 9/2007 | Shammai | 73/152.24 |
| 2009/0308600 A1 * | 12/2009 | Hsu et al. | 166/250.01 |

OTHER PUBLICATIONS

Australian Examination Report Dated Oct. 11, 2013; Australian Application No. 2010355265 (3 p.).

* cited by examiner

US 9,297,255 B2

NON-INVASIVE COMPRESSIBILITY AND IN SITU DENSITY TESTING OF A FLUID SAMPLE IN A SEALED CHAMBER

CROSS-REFERENCE TO RELATED APPLICATIONS

This application is a 35 U.S.C. §371 national stage application of PCT/US2010/039050 filed Jun. 17, 2010, which is incorporated herein by reference in its entirety for all purposes.

BACKGROUND

An application of formation fluid testing is to confirm the mobile fluid phase in the reservoir. This determination can be important in reservoirs in which there is significant uncertainty about the formation water salinity. This situation is further complicated in poor permeability reservoirs where there can be a long oil-water transition zone. Defining the mobile fluid phase down the transition zone can be achieved by sampling with, for example, a pump-out wireline formation tester (PWFT). This tool incorporates downhole sensors to analyze the fluid while pumping, the results of which are used to determine when and how to sample the formation fluid. The fluid samples are received into sample chambers.

After the sample chambers are retrieved to the surface, the chambers typically are sent to a lab for transfer of the sampled fluid and detailed analysis. Often, there is a long delay between retrieving the sample chambers and obtaining the analysis results; at times the delay can be on the order of weeks. Such delays are undesirable given the high costs associated with drilling operations.

BRIEF DESCRIPTION OF THE DRAWINGS

For a detailed description of exemplary embodiments of the invention, reference will now be made to the accompanying drawings in which.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The embodiments disclosed herein are directed to surface testing of a sealed sample chamber containing a fluid sample obtained downhole from the formation. The fluid sample is received into the sample chamber and held at in situ pressure inside the sample chamber (i.e., pressure of the fluid while in the formation). The surface testing is relatively quick, noninvasive (i.e., testing is performed without opening the sample chamber) and includes a determination of either or both of the fluid sample's in situ density and compressibility. The testing is performed in an automated fashion (i.e., with little or no human involvement) by a computer-operated testing system. The testing is performed without opening the sample chambers. Once the testing is complete at, for example, the rig site, the sample chambers can be sent to a lab for further testing.

The sample chambers for which the surface testing is performed generally comprise a cylindrical container containing one or more pistons that seal against the inner wall of the container and can be moved from one end of the container to the other. Some sample chambers have only a single piston while other sample chambers have two pistons. Some sample chambers include a buffer fluid (air, water, nitrogen, etc.). The operation of the sample chambers varies with the various types of chambers and the embodiments disclosed herein for determining density and compressibility are effected by the various chamber designs. Accordingly, the following discussion includes an overview of various sample chamber designs, followed by an explanation of the preferred embodiments of a testing system.

Figure 1:
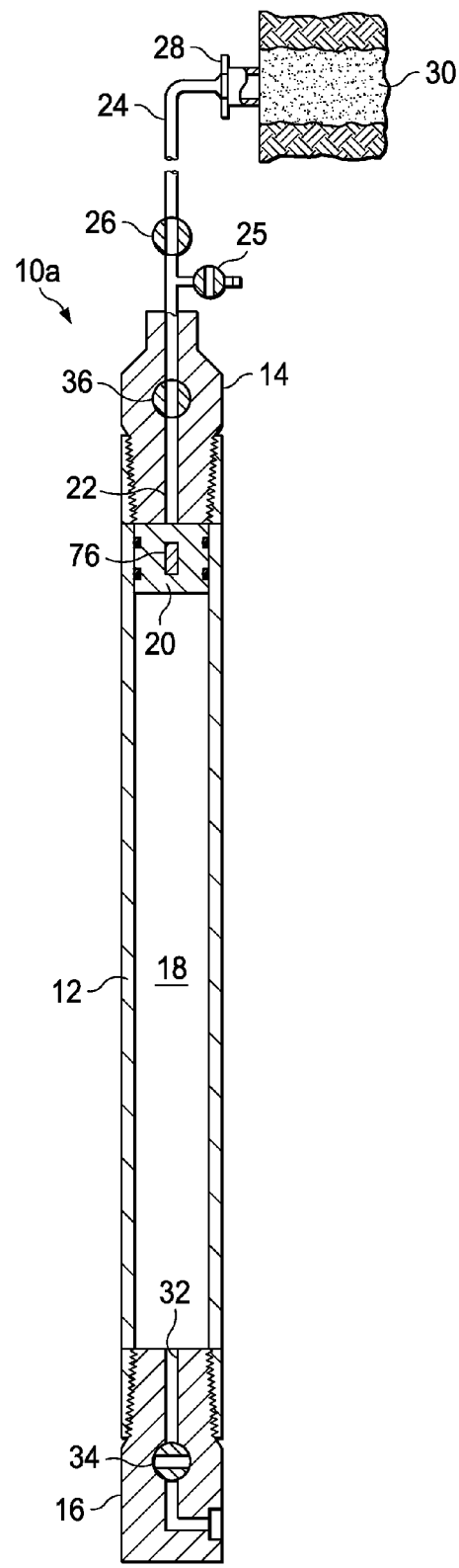
FIG. 1 illustrates an embodiment of sample chamber.

Four illustrative sample chambers are shown and discussed below with regard to FIGS. 1-4. FIG. 1 illustrates a downhole fluid sample chamber 10 including a sleeve-shaped cylinder 12 which forms an interior fluid compartment 18 therein. Cylinder 12 is substantially closed by an upper end cap 14 and lower end cap 16, with compartment 18 between the end caps and initially containing low pressure air that fills compartment 18 through valve 34 which is then closed to trap the air in the compartment 18. A separator piston 20 (also referred to herein as a "filling piston") movably sealed to the cylinder 12 initially is positioned in the upper end of the cylinder adjacent the end cap 14. When the sample chamber 10 is used in a well to collect a sample, and in response to the fluid sample pressure being greater than the air pressure in chamber 18, the separator piston 20 moves downward, thereby compressing the air which causes the pressure of the air to increase. The separator piston 20 movies downward until the air pressure on the lower side of the piston in compartment 18 is substantially equal to the pressure of the fluid sample on the upper side of the piston (between the piston and upper end cap 14). With the pressures substantially equal, the piston 20 will reside between the upper end cap 14 and lower end cap 16, and generally slightly above the lower end cap 16.

The upper end cap 14 includes a fluid passageway 22 therein for transmitting formation fluid into the cylinder 12 and to the top side of the separator piston 20. An isolation valve 36 is located along the flow path 22 in the upper end cap 14. Valve 36 is closed once the fluid sample is obtained. A fluid line 24 extends from the upper end cap 14 to the formation of interest 30, and an electronic flow line control valve 26 is positioned along the flow line 24 for controlling the fluid flow from the formation to the sampling cylinder. FIG. 1 further illustrates an annular packer element 28 for sealing engagement with the face of formation 30, so that formation fluid passes through the center of packer element 28 and to the flow line 24, and then to the cylinder 12. The lower end cap 16 also has a flow line 32 therein which communicates between the compartment 18 and exterior of the cylinder 12, with a normally closed valve 34 controlling the release of fluid along the flow line 32.

A valve 25 extends from line 24. The valve 25 remains closed when the tool is downhole. A pressure gauge (not shown) may be fluidly connected to the outlet of the valve 25 at the surface, and the valve 25 briefly opened to determine the pressure of the test fluid in the cylinder 12.

The fluid compartment 18 within the cylinder 12 thus initially serves as an air chamber for atmospheric air. To collect a formation fluid sample, the flow line control valve 26 is open to introduce formation fluid into the interior of the cylinder 12, thereby forcing the piston 20 downward. As the piston 20 moves downward toward the lower end cap 16, the air between piston 20 and the lower end cap 16 becomes increasingly compressed. Formation fluid at in situ (formation) pressure, fills the compartment 18 between piston 18 and upper end cap 14. Once the pressure of the compressed air below the piston 20 and the fluid sample above the piston 20 are at substantially the same pressure, the piston 10 stops moving and the flow line control valve 26 may be closed, thereby trapping the collected fluid sample within the cylinder 12.

Figure 2:
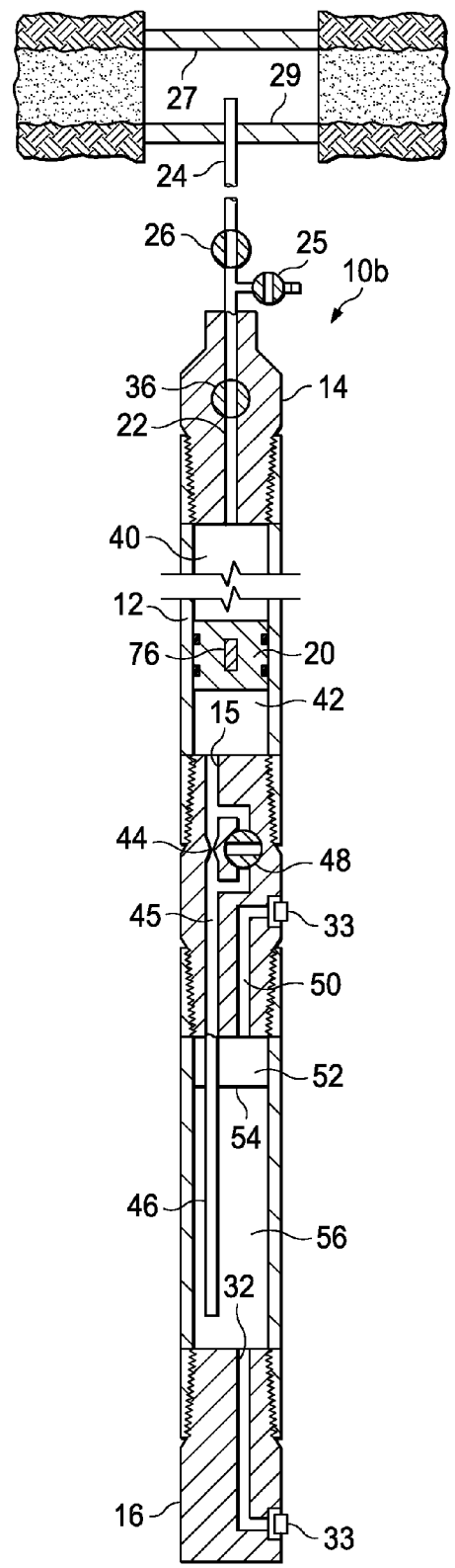
FIG. 2 illustrates another embodiment of a sample chamber.

FIG. 2 illustrates an alternate sample chamber 10b wherein water, ethylene glycol, oil, or another selected incompressible fluid may be used as a buffer fluid. The flow line 24 may be as discussed above in FIG. 1 to provide fluid communication with the interior of the cylinder 12. In the embodiment of FIG. 2, an upper packer 27 and a lower packer 29 are used to isolate fluid within formation 30 from the remainder of the wellbore. Any of the embodiments shown in FIGS. 1-4 may be used with the packer element 28 as shown in FIG. 1 or the straddle packers 27 and 29 shown in FIG. 2. Central member or choke sub 15 is fixed within the cylinder 12. The separator piston 20 initially may be positioned substantially adjacent the upper end cap 14, with the space between the piston 20 and the central member 15 being filled with water. The space below the member 15 and the lower end cap 16 may initially be filled with air at atmospheric pressure. A vent tube 46 may pass water from above the central member 15 to an area below the central member 15 and through a choke 44 positioned along the flow path 45 within the member 15. A bypass valve 48 may be used at the surface to recycle the chamber and for piston management. Flow line 50 fluidly connects the chamber below the central member 15 to the exterior of cylinder 12. Both the flow line 32 in lower end cap 16 and the outlet from flow line 50 in the central member 15 may each be closed by a plug 33.

When the flow line control valve 26 is open, formation pressure acts on the separator piston 20 and forces the buffer fluid, which, as noted above, may be water, ethylene glycol, oil or another selected incompressible liquid, through the restriction or choke 44, thereby establishing a threshold flowing pressure at which the formation fluid enters the chamber. The chamber 56 below the central member 15 and above the lower end cap 16 may be referred to as a choke chamber. Formation fluid forces the water through the choke and into the air filled (or gas filled) choke chamber 56, thereby compressing the air. Space 52 below central member 15 may thus be compressed air, with the interface 54 shown between the compressed air and the liquid. The separator piston 20 continues to move downward until the pressure of the compressed air is approximately equal to the pressure of the sample fluid from the formation. The flow line control valve 26 then may be closed to trap the collected fluid sample within the cylinder 12.

Figures 3, 4:
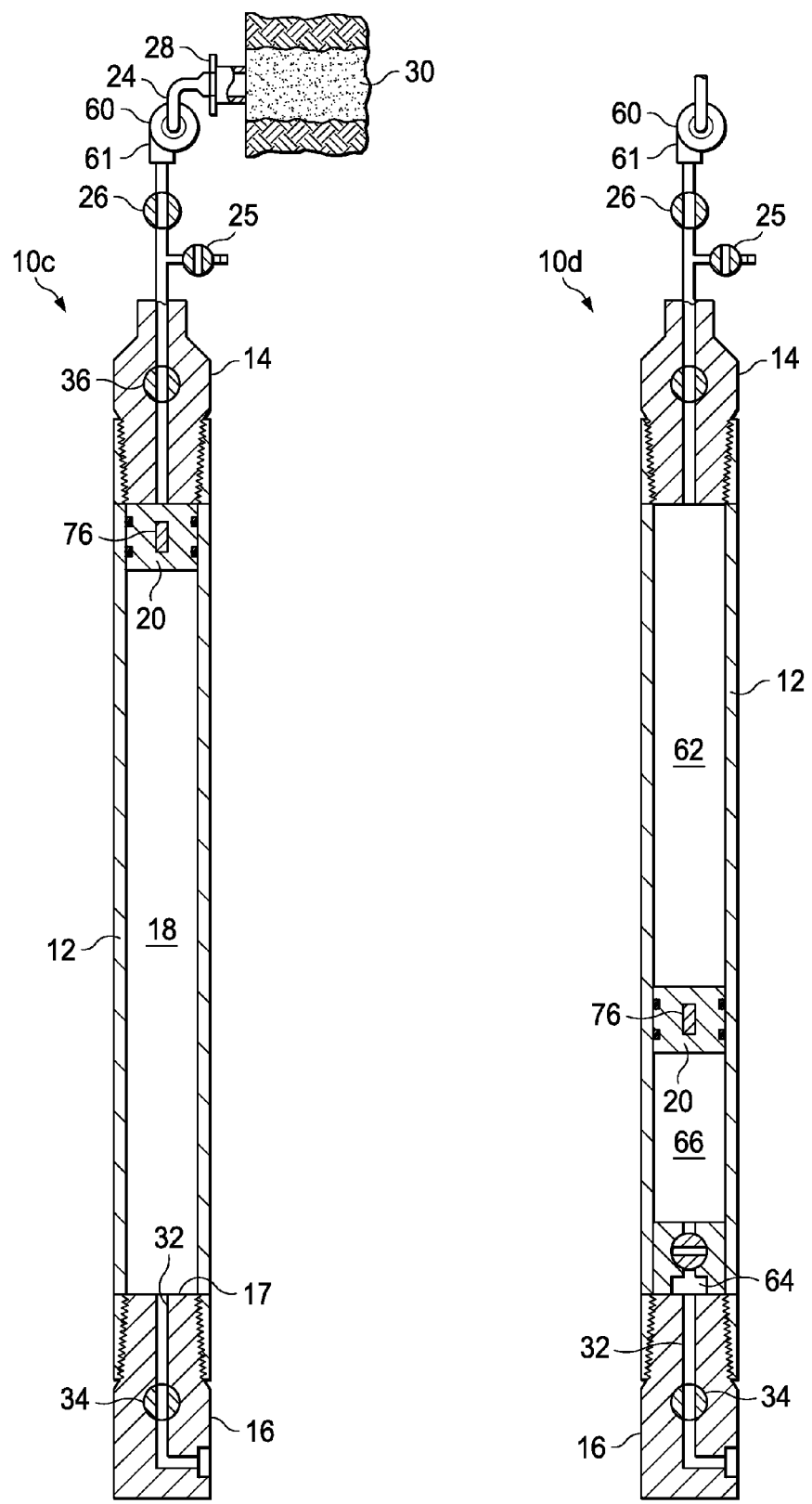
FIG. 3 illustrates yet another embodiment of a sample chamber.
FIG. 4 illustrates a further embodiment of a sample chamber.

Referring now to FIG. 3, an embodiment of yet another sample chamber 10c is shown. In this embodiment, a downhole pump 60 is included, with the inlet of the pump 60 connected to the downhole formation of interest 30 and the outlet of the pump 60 connected to the cylinder 12. In such embodiments, a tool string includes the pump 60 and multiple (e.g., 15) sample chambers 10c. Each sample chamber 10c has an associated electronically controlled valve 26 that, when opened, connects the pump 60 to that particular sample chamber. Initially, the piston 20 may be provided in the upper portion of compartment 18 adjacent the upper end cap 14. Valve 34 within the lower end cap 16 is open. Accordingly, the lower side of the piston 20 is exposed through open valve 34 to wellbore fluid at hydrostatic pressure. Downward motion of the piston 20 continues until piston 20 reaches its full extent of travel and rests against the upper surface 17 of the lower end cap 16. At that point, valves 34 and 36 are closed.

FIG. 4 illustrates yet another configuration for a sample chamber 10d which utilizes a compressible gas (e.g., nitrogen) that is pressurized to downhole conditions to compensate for sample contraction upon cooling. A pump 60 and valves 26 and 25 are provided as with the prior embodiment. The separator piston 20 thus is initially positioned adjacent the upper end cap 14, and nitrogen gas is contained in the space 66 between the separator piston 20 and a separate charging piston 64, which is sealed to cylinder 12 and does not pass fluid through piston 64. Wellbore fluid at hydrostatic pressure is exposed to the lower side of the charging piston 64 as valve 34 is open to provide fluid flow along the flow line 32 in the lower end cap 16. The outlet from the downhole pump 60 is directed to the cylinder 12, and as the compartment 62 (between the separator piston 20 and upper end cap 14) is filled with the fluid sample from the formation, the separator piston 20, the nitrogen gas and the charging piston 64 are pushed downward until the charging piston 64 reaches its full extent of travel, as shown in FIG. 4. Additional pumping moves the separator piston 20 further downward, compressing the nitrogen charge. Once overpressurized to the desired level, the flow line control valve 26 may be closed thereby trapping the collected sample within the sample chamber.

In each of the embodiments of FIGS. 1-4, the separator (filling) piston includes a magnet 76. The magnet 76 is supported on the separator piston 20, and preferably positioned within the separator piston. Due in part to the corrosive nature of the fluids contained within the cylinder 12, the cylinder 12 and the piston 20 preferably are fabricated from a high nickel alloy, such as inconel 718 or a titanium alloy. Besides being corrosion resistant, these materials are relatively non-magnetic. The magnet 76 within the piston 20 may be disk shaped, and typically may be an Al—Ni—Co or Sm—Co material. The magnet 76 is fixed coaxially within the separator piston 20 and is magnetized along its axis, which is substantially coaxial with the axis of the cylinder 12.

The embodiments of FIGS. 3 and 4 include the use of downhole pump 60 with the sample chambers. The downhole pump 60 preferably includes a filling sensor 61 such as a potentiometer that produces a signal indicative of the volume of fluid pumped by the pump 60 into the sample chamber. Once pumping ceases, the filling sensor's value is read and transmitted to the surface via, for example, wireline or mud-pulse techniques for recording by a test system (discussed below). The embodiments of FIGS. 1 and 2 do not use a pump and a different technique (discussed below) is used to determine the volume of the captured fluid sample. This latter technique can be used as well even in the embodiments in which a pump 60, and associated filling sensor, is available.

Figure 5:
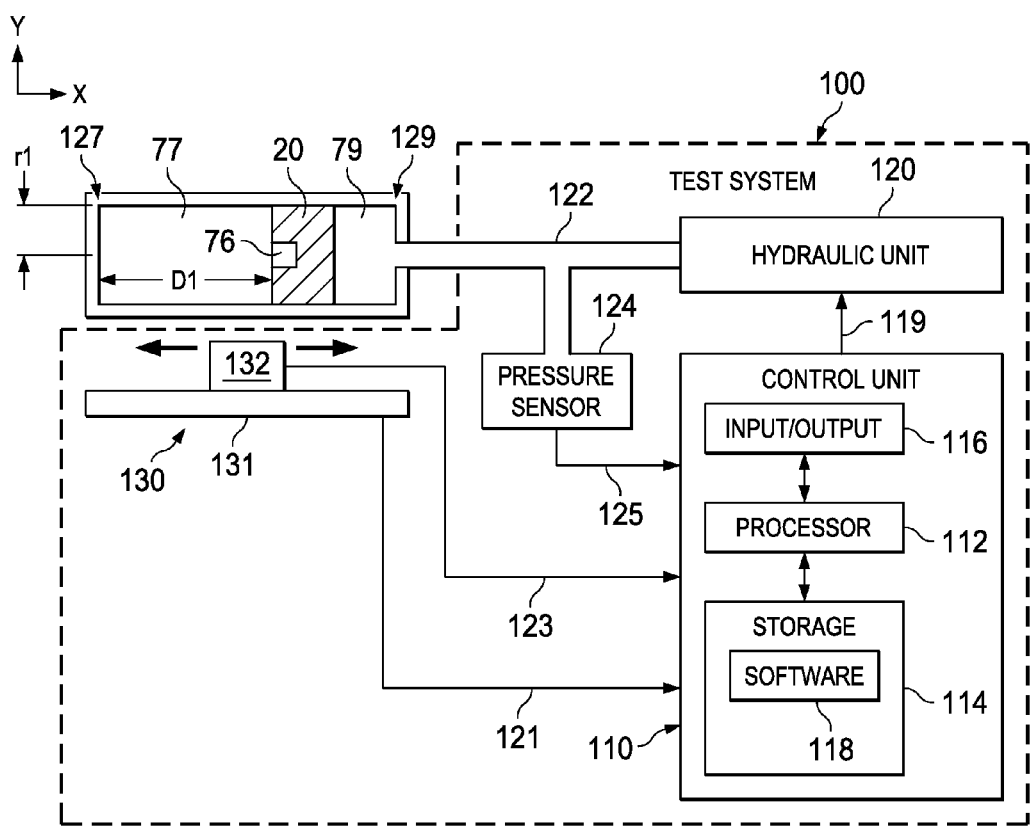
FIG. 5 provides a block diagram of test system in accordance with the preferred embodiments.

FIG. 5 shows a preferred embodiment of a test system 100. FIG. 5 also shows a sample chamber 10 (which can be any suitable sample chamber such as any of the chambers 10a-10d of FIGS. 1-4) loaded into the test system 100. Test system 100 may be located, for example, at the surface. The sample chamber 10 may reside, for example, on a support structure. As shown, the test system 100 comprises a control unit 110 coupled to a hydraulic unit 120 and to a linear position device 130. The control unit 110 may be, for example, a computer. The control unit 110 comprises a processor 112 coupled to a computer-readable storage medium 114 that contains executable software 118. The computer-readable storage medium 114 may comprise volatile memory (e.g., random access memory) or non-volatile storage (e.g., hard disk drive, flash storage, CD ROM, etc.). The software 114 is executed by processor 112 and, as such, causes the processor to perform, or at least initiate, some or all of the functionality described herein attributed to the test system 100 and/or control unit 110. One or more input/output (I/O) devices 116 are also included and coupled to the processor 112. Such I/O devices may include, for example, a keyboard, a mouse, a touchpad, a display, etc.

The hydraulic unit 120 comprises a hydraulic pump that is connectable to the sample chamber 10 via a hydraulic line 122. The hydraulic unit 120 can vary the pressure inside the hydraulic line in accordance with a signal 119 from the control unit 110. The control unit 110 thus can cause the hydraulic unit 120 to increase or decrease the pressure in the hydraulic line. The content of the hydraulic line may be a gas such as nitrogen, but other suitable hydraulic gasses or fluids may be used as well.

A pressure sensor 124 is provided on the hydraulic line 122. The pressure sensor 124 produces an electrical signal 125 that is proportional to the pressure in the hydraulic line 122. Signal 125 is provided to the control unit 110 which can monitor the pressure in the hydraulic line via the pressure sensor 124.

The linear position device 130 determines the location of the piston 20 within the sealed sample chamber. The linear position device 130 comprises a sensor locating device 131 and a magnetic field sensor 132 which can move along or near the exterior surface of the sample chamber 10 in the x-direction between one end 127 of the sample chamber and the other end 129. The magnetic field sensor 132 is sensitive to the magnetic field emanating from the piston's magnet 76. The magnetic field sensor 132 preferably comprises a Hall sensor, magnetoresistive sensor, fluxgate field sensor, induction coil sensor, induction coil gradiometer, or other suitable type of sensor. The sensor 132 may have single axis or multi-axis sensitivity. Further, the electrical signal 123 from the magnetic field sensor 132 is provided to the control unit 110.

The sensor locating device 131 is able to determine the position of the magnetic field sensor 132 and produce a signal 121 that encodes the sensor's position. The signal 121 is referred to as the position signal. The sensor locating device 131 determines the position of the sensor 132 via any of a variety of techniques. For example, the sensor locating device 131 may comprises a linear potentiometer, a laser distance sensor, an ultrasonic distance meter, a digital ruler, a draw wire sensor, etc.

In some embodiments, the voltage level of the position signal 121 from the sensor locating device 131 may vary from a lower voltage (e.g., 0V) to a higher voltage (e.g., 5V). The lower voltage corresponds to the sensor 132 being at one end of its travel path (i.e., at one end of the sample chamber 10), while the upper voltage corresponds to the sensor being at the opposing end of its travel path (i.e., at the other end of the sample chamber). A voltage halfway between the lower and higher voltages corresponds to the mid-point of the sample chamber. Thus, in such embodiments, the voltage level from sensor 132 correlates to location/distance along the length of the sample chamber.

Figure 6A:
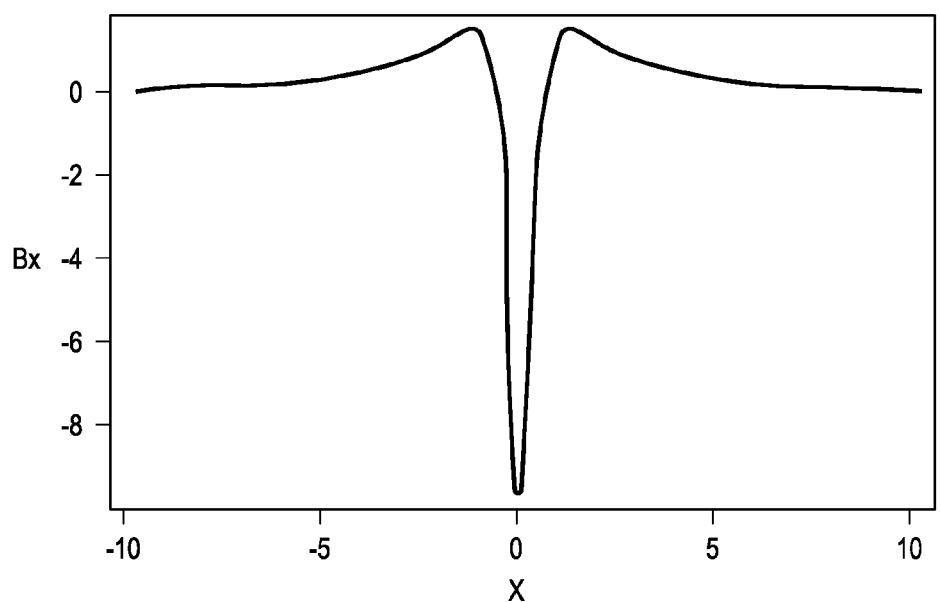
FIGS. 6a and 6b depict magnetic fields associated with a magnet provided on a piston internal to the sample chamber.
Figure 6B:
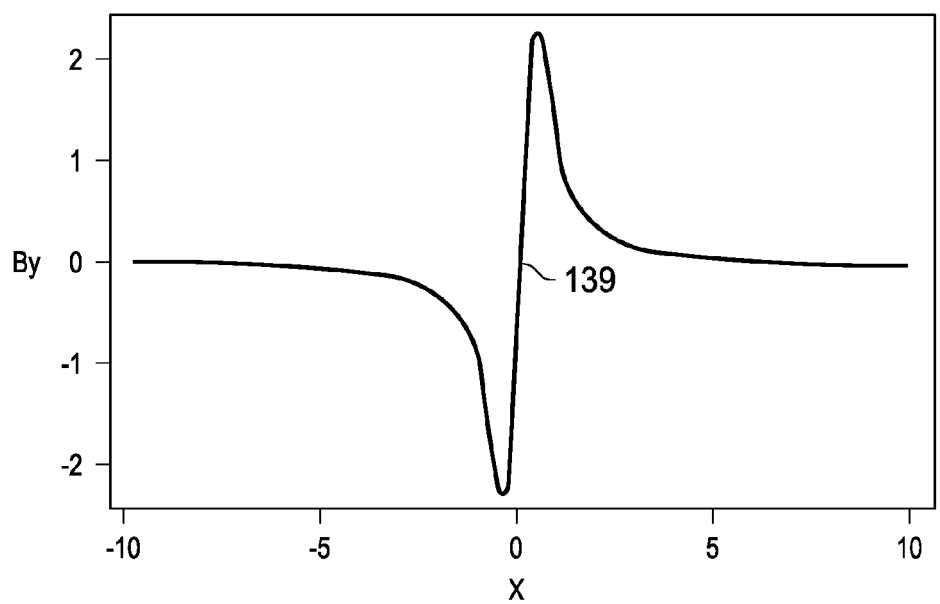

In accordance with a preferred embodiment, the magnet 76 is installed in or on the piston 20 such that the magnet's north pole is pointed in the x-direction. The strength of the magnetic field emanating from magnet 76 varies with respect to location along the line of travel in the x-direction of the magnetic field sensor 132. The x- and y-components of the magnetic field from magnet 76 are depicted in FIGS. 6a and 6b, respectively. The x-component of the magnetic field depicted in FIG. 6a shows that the x-component of the magnetic field has an absolute value that is a maximum at x=0, which corresponds to the location of the magnet 76 and thus the piston 20. That is, as the magnetic field sensor 132 sweeps from one end of the sample chamber to the other, the detected magnetic field (x-component) is a maximum (in absolute value) when the sensor 132 is adjacent the magnet 76. The magnetic field sensor 132 produces an electrical signal 123 that is provided to the control unit 110 which thus is able to monitor the magnitude of the sensor's signal 123 to detect the peak in the detected magnetic field. Once the magnetic field peak is detected, the control unit 110 reads the position signal from the sensor locating device 131 to determine the sensor's position corresponding to the peak of the magnetic field. From that position, the control unit 110 is able to determine the distance D1 the piston 20 is within the sealed chamber from end 127.

FIG. 6b depicts the y-component of the magnetic field from magnet 76. In some embodiments, the magnetic field sensor 132 has sensitivity in the y-direction instead of, or in addition to, the x-direction In such embodiments, the control unit 110 can determine when the magnetic field sensor 132 is adjacent the magnetic 76, and thus piston 20, by determining when the y-component of the magnetic field crosses through 0 at point 139. As explained above, when the control unit 110 determines that the sensor 132 is adjacent the magnet 76, the control unit 110 reads the position signal from the sensor locating device 131 to determine the sensor's position corresponding to the peak magnetic field. From that position the control unit 110 is able to determine the distance D1 the piston 20 is within the sealed chamber from end 127.

Depending on whether a single-axis or multi-axis magnetic field sensor 132 is used, the control unit 110 determines when the sensor 132 is adjacent the magnet 76 using the x-component of the magnetic field, the y-component of the magnetic field, or a combination of both. If both the x- and y-components are used, the magnetic field sensor 132 provides two signals to the control unit 110—one signal corresponding to each magnetic field component. The control unit 110 may, for example, use one signal as confirmation that the other signal is accurately indicating magnet 76 location. Alternatively, the control unit 110 may average the times at which the control unit 110 determines the magnet location from both signals and determine the piston location using the position signal 121 from the sensor locating device 131 corresponding to the computed average time value.

In accordance with various embodiments, the sample chamber is cylindrical. The volume of a cylinder is computed as $D\pi r^2$ where D is the length of the cylinder and r is its cross-sectional radius. Referring to FIG. 5, the collected fluid sample is in the portion 77 of the sample chamber between the piston 20 and sample chamber end 127. The volume of that portion and thus the volume of the fluid sample is $(D1)(\pi r_1^2)$ where $r_1$ is the cross-section radius of sample chamber 10. The radius $r_1$ is known ahead of time and distance D1 is determined by the control unit 110 by reading the magnetic field sensor 132 and sensor locating device 131.

FIGS. 7-10 illustrate various method embodiments. The order of the actions depicted in these methods may be as shown in the figures or may be different from that shown. Further, not all of the actions are necessarily performed sequentially. Instead, two or more actions may be performed in parallel.

Figure 7:
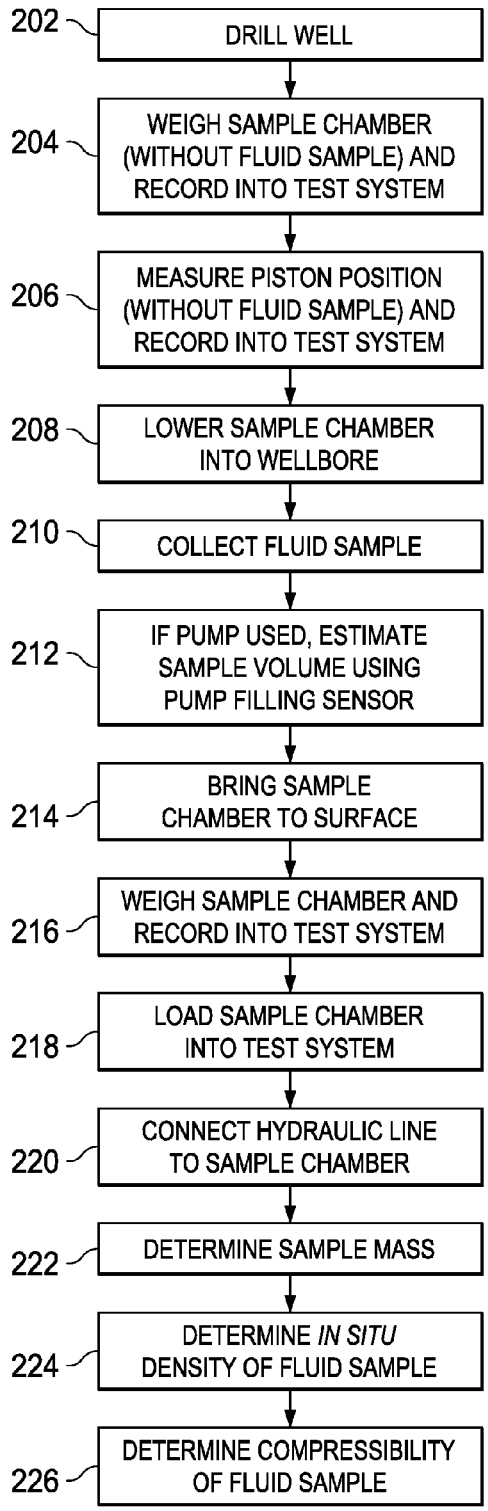
FIG. 7 shows a method embodiment in which a fluid sample is collected and tested at the surface for in situ density and compressibility.

In FIG. 7, well drilling begins at 202. The drilling operation may comprise any type of drilling such as vertical, deviated or horizontal drilling, multi-lateral drilling, or conventional drilling or under-balanced drilling. During the drilling phase, various types of tests may be performed using wireline, measurement while drilling (MWD), logging while drilling (LWD), etc. The testing described herein can be with any such type of testing paradigm.

At 204, a sample chamber 10 is weighed at the surface and thus before a fluid sample is collected. The chamber's weight is recorded into the test unit 100 (e.g., the control unit 110). At 206, the sample chamber 10 is placed into the test system 100 and the piston's position is determined and also recorded into the test system 100 (e.g., in storage 114). This "initial" piston position thus is the position before a fluid sample is taken. At 208, the sample chamber 10 is lowered down the well bore and a fluid sample is collected at 210.

If a downhole pump 60 is used (e.g., as with the sample chamber embodiments of FIGS. 3 and 4) and such a pump includes a filling sensor as explained above, at 212 the pump measures or estimates the sample volume which may be transmitted to the surface via wireline or mudpulse communication techniques as noted above. The sample chamber 10 is brought up to the surface at 214 and, at 216, the sample chamber 10 is again weighed. The post-sample weight of the sample chamber 10 is recorded into the test system. The difference in the before and after weights of the sample chamber corresponds to the weight/mass of the fluid sample itself.

At 218, the sample chamber 10 is loaded into the test system and, at 220, the hydraulic line 122 is connected to the sample chamber. At 222, the control unit 110 determines the mass of the fluid sample by, for example, subtracting the initial (no sample) weight of the sample chamber from the weight of the chamber containing the fluid sample. The mass may be stored in storage 114. At 224, the control unit 110 determines the in situ density of the fluid sample in the sealed sample chamber.

Figure 8:
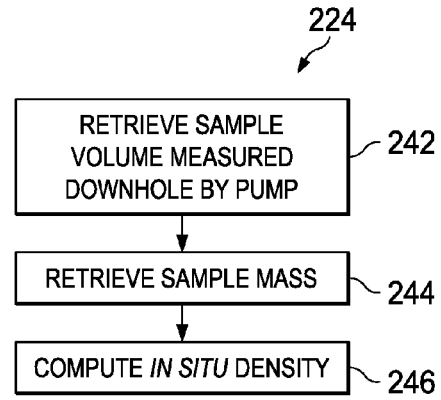
FIG. 8 shows an illustrative method embodiment for determining in situ density of a fluid sample in a sealed chamber.
Figure 9:
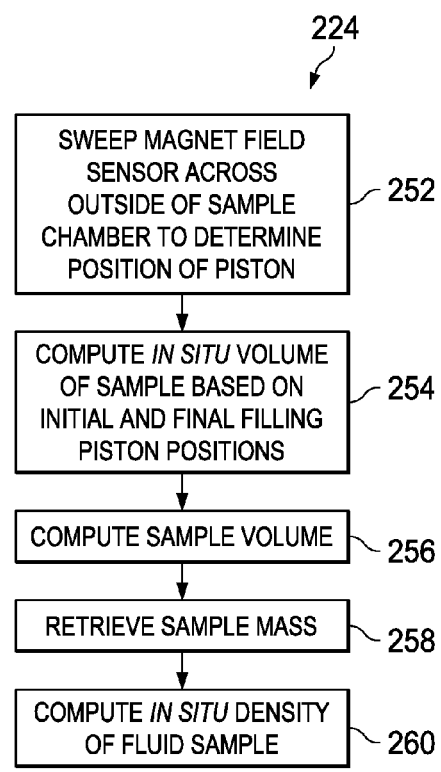
FIG. 9 shows another method embodiment of the determination of in situ density of the fluid sample.
Figure 10:
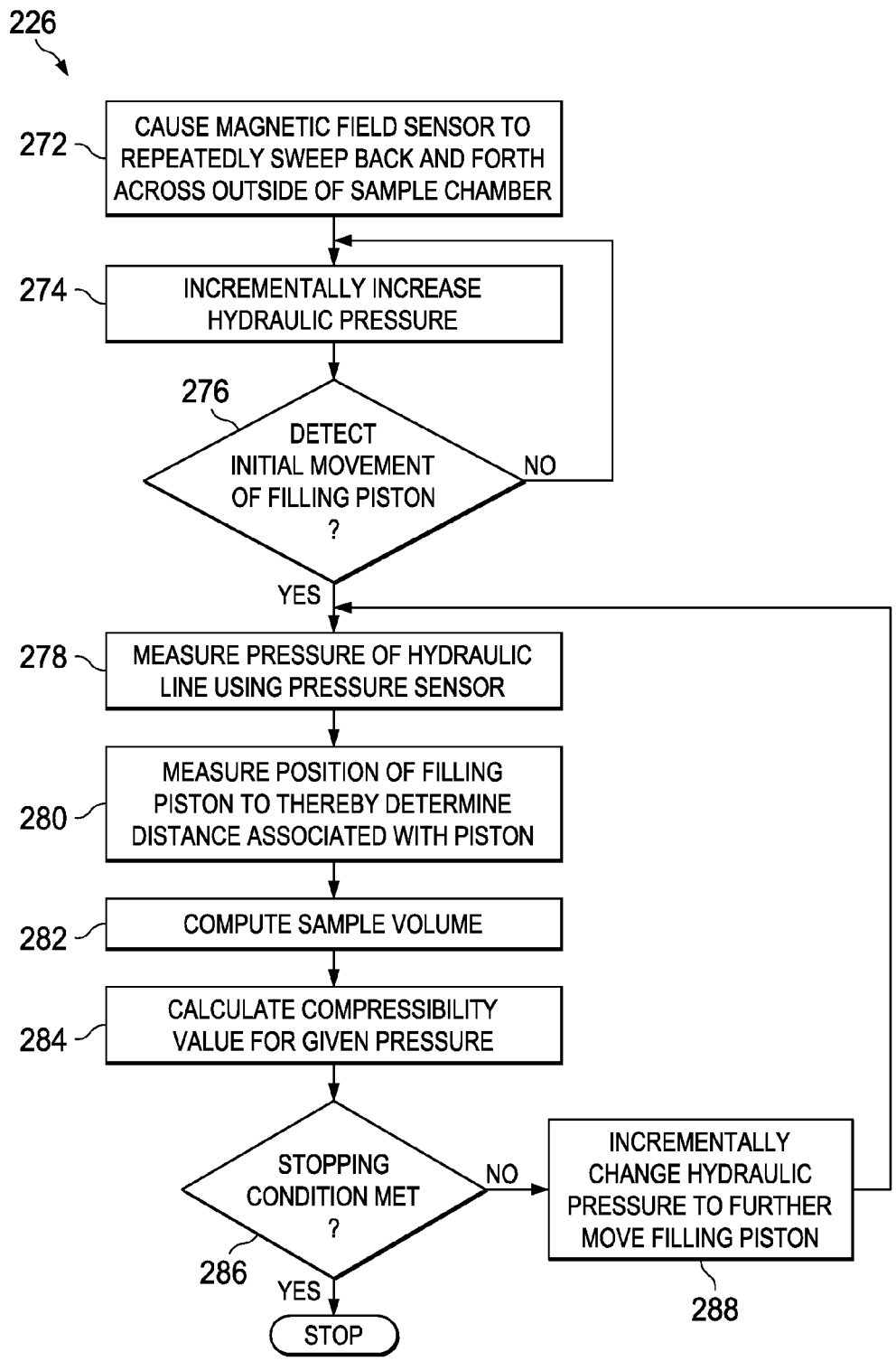
FIG. 10 shows a method embodiment for determining fluid sample compressibility.

FIGS. 8 and 9 illustrate two embodiments for determining the in situ density of the fluid sample. At 226, the control unit 110 determines the compressibility of the fluid sample and FIG. 10 illustrates a technique for determining compressibility.

FIG. 8 illustrates an embodiment 224 for determining in situ density. This embodiment is particularly useful if a downhole pump was used to fill the sample chamber. At 242, the control unit 110 retrieves the sample volume as measured or estimated by the downhole pump 60 and transmitted to surface as explained above. At 244, the control unit retrieves the sample mass as well. At 246, the control unit divides the mass by the volume to compute in situ density.

FIG. 9 illustrates an alternative embodiment 224 for determining in situ density, particularly if downhole pump 60 is not used or, if a pump is used without the ability to measure or estimate sample volume. At 252, the control unit 110 causes the magnetic field sensor 232 to begin sweeping across the outside of the sample chamber 10 to determine the position of the piston 20. The position of the piston 20 informs the control unit 110 as to the distance D1. Using distance D1, at 254 the control unit 110 computes the in situ sample volume. In some embodiments, in situ volume is based on both the initial piston position (FIG. 7, 206) before the fluid sample is collected and the final piston position (252). Specifically, the distance D1 is computed to be the difference between the initial and final piston positions. Computing the difference in initial and final piston positions is useful if a gas was included in the compartment in which the sample fluid is subsequently collected—the total volume of the compartment containing the sample fluid is the volume of both the sample fluid and the volume of the initial gas and thus should be compensated for the volume of the gas for greater volume accuracy.

At 256, the control unit 110 computes the sample volume as explained above. At 258, the control unit 110 retrieves the sample mass from storage 114 and, at 260, the in situ density is computed by, for example, dividing the sample mass by the sample volume.

FIG. 10 provides a method embodiment 226 in which compressibility of the fluid sample is determined. In general, the piston 20 is moved within the sample chamber 10 to various positions thereby applying different pressures on the fluid sample. The volume of the fluid sample is determined at each pressure setting. At 272, the control unit 110 preferably causes the magnetic field sensor to repeatedly sweep back and forth across the outside of the sample chamber 10 along the x-direction. At 274, the control unit 110 asserts a signal to the hydraulic unit 120 to cause the hydraulic unit thereby to incrementally increase the pressure in the hydraulic line 122. Referring briefly to FIG. 5, the hydraulic fluid in the hydraulic line 122 is in fluid communication with space 79 behind the piston 20. Thus, an increase in pressure in the hydraulic line 122 is also asserted against the piston 20. Until the pressure of the hydraulic fluid in space 79 exceeds the pressure of the fluid sample in space 77, the piston 20 will not move toward end 127 of the chamber 10. Thus, at 276, the control unit 110 monitors the signals 121 and 123 from the linear position device 130 to detect movement of the piston 20. The pressure at which the piston 20 begins to move is referred to as the "opening pressure." Once the opening pressure is reached, increasing the hydraulic pressure further causes the piston 20 to move toward end 127 of the chamber 10. Further, for each such hydraulic pressure in excess of the opening pressure, the piston will move to and stop at a certain point within the chamber 10; that point is the location at which the hydraulic pressure substantially equals the pressure of the fluid sample (which itself experiences an increases in pressure as the piston 20 increasingly compresses the fluid sample).

If piston movement is not detected at 276, then control loops back to 274 at which the hydraulic pressure is again incremented (e.g., in increments of 100 psi). Once piston movement is detected, however, control passes to 278 at which the control unit 110 records the pressure of the hydraulic line as measured by pressure sensor 124. Because hydraulic pressure of line 122 is substantially equal to the fluid sample pressure, the pressure measured by pressure sensor 124 is also the pressure of the fluid sample.

At 280, the control unit also measures the position of filling piston 20 thereby to determine distance D1 associated with piston 20. Preferably, distance D1 is computed as the difference between the newly measured piston distance and its initial distance before the fluid sample was collected (FIG. 7, 206). At 282, using newly determined distance D1 and the known radius of the cylindrical sample chamber 10 (or, in general, known cross-sectional area of chamber if the chamber has a shape other than cylindrical), the sample volume is computed by control unit 110 as the cross-sectional area times D1.

At 284, the control unit 110 computes the fluid sample compressibility for the current sample pressure. Compressibility is defined as the fractional change of volume due to changes in pressure for a constant temperature and is estimated using the following equation:

$$\text{Comp} = -\frac{1}{V}\left(\frac{\partial V}{\partial p}\right)_T$$

where V is the total volume of the sample chamber 10 and T is a constant temperature. The control unit 110 calculates and stores and/or displays a compressibility value for each pressure measured at 278.

At 286, the control unit 110 determines whether a stopping condition is met. In some embodiments, the stopping condition may comprise a threshold pressure level (e.g., 10,000 psi). If the stopping condition has not been reached, then control passes to 288 in which the control unit 110 causes the hydraulic unit 120 to incrementally change (e.g., increase) the hydraulic pressure in hydraulic line 122 to further move piston 20 to thereby further compress the fluid sample in space 77. The increment in pressure may be in increments of, for example, 500 psi. The process loops back to 278 for another pressure measurement, and so on. If, at 284, it is determined that the stopping condition has been met, then the process stops at 290.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method, comprising:
    changing a hydraulic pressure applied to a floating piston within a sealed sample chamber such that the pressure on each side of the piston is substantially equal, said sample chamber containing a formation fluid sample;
    measuring said hydraulic pressure with a pressure sensor external to said sample chamber;
    measuring a distance associated with said piston with a magnetic sensor; and
    computing compressibility of said formation fluid sample contained within said sealed sample chamber based on the distance and the measured hydraulic pressure.

2. The method of claim 1 wherein before measuring the hydraulic pressure, increasing the hydraulic pressure until movement of the piston is detected.

3. The method of claim 1 further comprising lowering said sample chamber downhole before changing the hydraulic pressure, measuring the hydraulic pressure, measuring the distance, and computing compressibility.

4. The method of claim 1 further comprising repeating each of changing the hydraulic pressure, measuring the hydraulic pressure, and measuring the distance associated with said piston at each such pressure.

5. The method of claim 4 wherein computing compressibility comprises computing compressibility based on a plurality of the measured distances associated with the piston at corresponding pressures.

* * * * *